(12) United States Patent
Lin (10) Patent No.: US 8,496,923 B2
(45) Date of Patent: *Jul. 30, 2013

(54) PROBIOTIC TREATMENT FOR INFECTIOUS GASTROINTESTINAL DISEASES

(75) Inventor: Jhy-Jhu Lin, Potomac, MD (US)

(73) Assignee: Imagilin Technology, LLC., Frederick, MD (US)

( * ) Notice: Subject to any disclaimer, the term of this patent is extended or adjusted under 35 U.S.C. 154(b) by 159 days.

This patent is subject to a terminal disclaimer.

(21) Appl. No.: 12/917,681

(22) Filed: Nov. 2, 2010

(65) Prior Publication Data

US 2011/0129518 A1      Jun. 2, 2011

Related U.S. Application Data

(60) Division of application No. 11/493,859, filed on Jul. 26, 2006, now Pat. No. 7,935,334, and a continuation-in-part of application No. 11/177,264, filed on Jul. 7, 2005.

(60) Provisional application No. 60/705,730, filed on Aug. 5, 2005, provisional application No. 60/585,941, filed on Jul. 8, 2004.

(51) Int. Cl.
| | | |
|---|---|---|
| *A01N 63/00* | (2006.01) | |
| *A01N 65/00* | (2009.01) | |
| *C12N 11/00* | (2006.01) | |
| *C12N 11/16* | (2006.01) | |

(52) U.S. Cl.
USPC ............... 424/93.45; 424/93.1; 435/174

(58) Field of Classification Search
None
See application file for complete search history.

(56) References Cited

U.S. PATENT DOCUMENTS

| | | | | |
|---|---|---|---|---|
| 5,840,318 A | * | 11/1998 | Marshall et al. | 424/282.1 |
| 6,500,463 B1 | * | 12/2002 | van Lengerich | 424/499 |
| 2002/0114786 A1 | * | 8/2002 | Fabre et al. | 424/93.3 |

* cited by examiner

*Primary Examiner* — Debbie K Ware
(74) *Attorney, Agent, or Firm* — Stein IP, LLC (57) ABSTRACT

An exemplary embodiment providing one or more improvements includes feeding animals with probiotic microbes encapsulated in a mixture of xanthan gum and chitosan, or in gelatin, specifically *Pediococcus acidilactici* and *Saccharomyces boulardii*. Such encapsulation protects the viability of the probiotic microbes against unfavorable temperatures. An exemplary embodiment providing one or more improvements includes methods of using viable probiotics in therapy of birds and mammals infected with infectious diseases. Probiotics acted as adjuvants in stimulating antibody reaction and stimulated a cellular immunity response. In particular, probiotics were shown to reduce the number of viable oocytes from fecal samples, stimulate antibody production, and stimulate of proliferation of splenocytes in chickens infected with *Eimeria*. In addition, probiotics were shown to relieve symptoms of parvovirus infection in dogs.

10 Claims, 6 Drawing Sheets

PROBIOTIC TREATMENT FOR INFECTIOUS GASTROINTESTINAL DISEASES

CROSS-REFERENCE(S)

This application is a divisional application of application Ser. No. 11/493,859 filed on Jul. 26, 2006, now U.S. Pat. No. 7,935,334 the entire disclosure of which is incorporated into this application by reference and to which the instant application claims priority. Co-pending application Ser. No. 11/493,859 further claims priority from provisional Application No. 60/705,730 filed Aug. 5, 2005, and is a continuation-in-part of application Ser. No. 11/177,264, filed Jul. 7, 2005, which further claims priority from provisional Application No. 60/585,941, filed Jul. 8, 2004.

STATEMENT REGARDING FEDERALLY SPONSORED RESEARCH OR DEVELOPMENT

Not Applicable.

REFERENCE TO A "MICROFICHE APPENDIX"

Not Applicable.

BACKGROUND

Description of Related Art Including Information Disclosed Under 37 CFR 1.97 and 37 CFR 1.98

Probiotics are described as "live microorganisms, which, when administered in adequate amounts, confer a health benefit on the host" (reports of the United Nations Food and Agricultural Organization and the World Health Organization, Alternative Medicine 2001). Probiotics are widely applied as nutritional supplements in animals and humans. For example, yeast is used as a nutrient supplement for livestock, and yogurt with lactic acid bacteria-Lactobacillus and/or Bifidobacterium is commonly used to prevent and cure diarrhea-related gastrointestinal (GI) infectious diseases (Alvaez, et al, 2001; Fuller 1989; Majamaa, et al 1995). Multiple unique properties of probiotics such as anti-infectious properties, immune modulatory effects, enhanced barrier functions, metabolic effects and alternations of intestinal mobility or function make probiotics an effective type alternative medicine for animals and humans (Walker and Buckley, 2006).

Although probiotic products like short chain fatty acids (SCFA), cell wall peptidoglycan and short chain DNA fragments containing CpG sequences can have beneficial probiotics effects, the administration of live microorganisms to animals and humans remain to be the core application and research studies of probiotics (Walker and Buckley, 2006). In order to have the maximum effects of probiotics on animals and humans, one has to administrate live bacteria to reach gastrointestinal tracts for multiplication (Kailasapatha and Chin 2000). Lactobacillus spp and Bifidobacterium spp are two most commonly probiotics described in scientific literature and in commercial products. Both Lactobacillus spp and Bifidobacterium spp are facultative anaerobic bacteria. Most species (or strains) of Lactobacillus and Bifidobacterium are sensitive to the exposure of oxygen (Gomes et al, 1995; Talwalkar and Kailasapathy, 2004) and high temperature. It is difficult to maintain the viability of Lactobacillus and Bifidobacterium at room temperature under consistent open and closure operations. Therefore, variable results are often described, especially for commercially available products that are required to have long term storage and shipping in various temperature (Tuomola et al., 2001).

U.S. Pat. No. 5,968,569 discloses a pet food product of a gelatinized starch matrix including a probiotic micro-organism. Specifically disclosed are Saccharomyces and Pediococcus acidilactici.

U.S. Pat. No. 6,551,633 discloses a milk based powder for pets which includes lactase and lactose. Also disclosed are the probiotic organisms of U.S. Pat. No. 5,968,569.

U.S. Pat. No. 6,780,447 discloses animal foods comprising sorbic acid and live or dead microorganisms. A very large number of species is disclosed including P. acidilactici.

U.S. Pat. No. 6,827,957 discloses animal foods of specific formulation having a soft inner component and a hard shell along with probiotics. Specifically, Saccharomyces is disclosed.

U.S. Pat. No. 6,835,397 discloses an encapsulated yeast including a variety of probiotics including Saccharomyces. boulardii and Pediococcus. acidilactic (sic).

US Pub. Pat. Applic. 2003/0049240 discloses a method for treating helicobacter infections including the use of Lactobacillus and Bifidobacterium.

US Pub. Pat. Applic. 2003/0109025 discloses methods for treating helicobacter infections including the use of Lactobacillus and Bifidobacterium.

US Pub. Pat. Applic. 2004/0197352 discloses a prebiotic composition which reduces creatine and BUN and includes a variety of microbial species.

US Pub. Pat. Applic. 2003/0165472 discloses a method for the storage and delivery of microorganisms.

US Pub. Pat. Applic. 2006/0008511, incorporated herein by reference, discloses probiotic microbes encapsulated in a mixture of xanthan gum and chitosan, or in gelatin.

REFERENCES

Alvaez, S., Herrero, C., Bru, E., Perdigon, G. 2001. Effect of Lactobacillus casei and yogurt administration on prevention of Pseudomonas aeruginosa infection in young mice. J. food Prot. 64: 1768-1774.

Dalloul, R. A., H. S. Lillehoj, J.-S. Lee, S.-H. Lee, and K.-S. Chung. 2006. Immunopotentiating effect of a Fomitella fraxinea-derived lectin on chicken immunity and resistance to coccidiosis. Poult. Sci. 85: 466-451.

Fuller, R. 1989. Probiotics in man and animals. A review. J. Appl. Bacteriol 66: 365-78.

Gomes A. M. P., Malcata F. X., Klayer F. A. M., Grande H. J. 1995 Incorporation and survival of Bifidobacterium sp. strain Bo and Lactobacillus acidophilus strain Ki in a cheese product. Netherlands milk and dairy journal vol. 49: 71-95.

Isolauri, E. 2003. Probiotics for infectious diarrhea. Gut 52: 436-437.

Kailasapatha K, Chin J. 2000. Survival and therapeutic potential of probiotic organisms with reference to Lactobacillus acidophilus and Bifidobacterium spp. Immunol Cell Biol. 78: 80-88.

Lillehoj, H. S., W. Min, and R. A. Dalloul. 2004. Recent progress on the cytokine regulation of intestinal immune responses to Eimeria. Poult. Sci. 83: 611-623.

Majamaa, H., Isolauri, E., Saxelin, M., Vesikari, T. 1995. Lactic acid bacteria in the treatment of acute rotavirus gastroenteritis. J. Pediatric Gastroenterol Nutr 20: 333-339.

Perdigon, G., Fuller, R., Raya, R. 2001. Lactic acid bacteria and their effect on the immune system. Curr Issues Intest Microbiol. 2(1): 27-42.

Talwalkar A, Kailasapathy K. 2004 The role of oxygen in the viability of probiotic bacteria with reference to *L. acidophilus* and *Bifidobacterium* spp. *Curr Issues Intest Microbiol.* 5(1): 1-8.

Tuomola, E., Crittenden, R., Playne, M., Isolauri, E., and Salminen, S. 2001 Quality assurance criteria for probiotic bacteria. Am J Clin Nutr 73(suppl): 393S-398S.

Walker, R. and Buckley, M., 2006 "Probiotic Microbes: The Scientific Basis" 2006

A report from the American Academy Microbiology, page 1-28. by Pensare Design Group.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following embodiments and aspects thereof are described and illustrated in conjunction with systems, tool and methods which are meant to be exemplary and illustrative, not limiting in scope. In various embodiments, one or more of the above-described problems have been reduced or eliminated, while other embodiments are directed to other improvements.

Embodiments disclosed include a preparation for pets comprising probiotic microbes encapsulated in a mixture of xanthan and chitosan gums. Embodiments disclosed include a preparation for pets comprising probiotic microbes encapsulated in a gelatin capsule. In embodiments the probiotic microbes comprise *Saccharomyces* yeast and lactic acid bacteria. In embodiments the probiotic microbes comprise yeast. In embodiments the probiotic microbes comprise lactic acid bacteria. In embodiments the yeast is *Saccharomyces*. In embodiments the lactic acid bacteria is *Pediococcus*. In embodiments the *Saccharomyces* yeast is *Saccharomyces cereviase boulardii* also termed *Saccharomyces boulardii*. In embodiments the lactic acid bacteria is *Pediococcus acidilactici*. In embodiments the xanthan gum concentration is from about 0.2 percent weight by volume to about 2 percent weight by volume and the concentration of chitosan gum is about 0.1 percent weight by volume to 1.0 percent weight by volume and the pH is from about 2 to about 7. In embodiments the xanthan gum concentration is from about 01.25 percent weight by volume and the concentration of chitosan gum is about 0.4 percent weight by volume and the pH is about 4.15. Embodiments include the process of treating infectious gastrointestinal disease in birds and mammals in need of such treatment which comprise the step of feeding the bird or mammal in need of treatment encapsulated probiotic microbes or include the probiotics in animal food or animal treats. Embodiments include the process of enhancing immune responses against antigens in birds and mammals which comprise the step of feeding the bird or mammal in need of treatment encapsulated probiotic microbes or include the probiotics in animal food or in animal treats.

DETAILED DESCRIPTION

Probiotics are the beneficial living bacteria that naturally exist in the gastrointestinal (GI) tracts of humans and animals. Probiotics are well accepted as the food supplements for human consumption. When patients have discomforts of digestive systems because of treatment with antibiotics or suffering form travel, doctors often recommend the patient to take probiotics to restore the microflora in patient digestive systems. Recently, the medical community increasingly recognizes probiotics as the agents that are able to enhance human immune responses for improving the efficacy of vaccine and for disease prevention. Probiotics are quickly regarded as one of the primary categories by the functional food industry. In farm animals such as pigs, cattle, dairy cows and poultry, probiotics are widely used as the substitutes for antibiotics as the growth promoters. Producers have recognized the beneficial effects of probiotics that not only improve the animal growth but also reduce the infection of enteric pathogens significantly. The beneficial effects of probiotics on pets (dogs, cats, and other small animals like guinea pigs) have attracted many researchers to investigate the mechanisms, and the research results were published in many journals. Today, pet food manufactures include probiotics as one of the important ingredients in many premium pet foods. Probiotics in capsules or chewable tablets for pet application are also commercially available. However, pet owners either are not familiar with probiotics or have experiences with the variable Probiotics effects on pets, and have doubts about the real functions of probiotics. Although the trends for human and farm animals have accepted probiotics as the nutrient supplements or as powerful neutraceutical products, pet owners are not fully aware that probiotics can contribute significant effects on pets in good health to expand their life span.

How do probiotics function as the beneficial effects on pets? Probiotics have to be able to travel along pet's GI tracts. When they have the opportunity to attach to GI tract surfaces, probiotic microorganisms can start to replicate. When probiotic microorganisms replicate and grow, they will decompose the food token by pets to produce acid compounds, which will create unfavorable acidic environments for most of GI tract pathogens to survive. Some of the probiotics also secrete the toxic compounds that are harmful to the pathogens. Moreover, as the probiotics attached to pet's GI tracts, they become generic immunogens, raise the antibody production and enhance the pet immune response for pathogen infections. As probiotic microorganisms multiply, they occupy the surfaces of GI tracts and prevent the possibility for the pathogens to attach to pet's GI tracts for infection. During the process of multiplications, Probiotics degrade the complex food compounds into the simple nutrition for pets to absorb and to utilize. This will not only help the pets to strengthen their bodies but also reduce the bad odors typically generated by pets caused either by the incomplete food digestions or by excess gas production through different digestion pathways. Therefore, in order to have the effects of probiotics on pets, the pet owners have to make sure to deliver the live probiotics into pet's GI tracts for microorganisms to multiply and to grow. It is critical to have the sources of viable probiotics for pet to uptake and to ensure the live probiotics that will be able to reach pet's GI tracts in order to make sure that the pet will have the beneficial effects of probiotics.

Let us take a close look of these two critical issues when we apply probiotics to the pets. By understanding these critical issues, we can easily find out why the pet owners experienced the variable effects of probiotics. If we go to a pet store, we may easily find many pet foods do include the probiotics, especially, probiotic fermentation cultures. Interestingly, Canadian scientists used to perform the extensive research survey for 19 commercially available pet foods, which claim to contain probiotics. They reported that no products contained all the listed probiotics, and average bacterial growth only ranged from 0 to $1.8 \times 10^5$ CFU/g (Colony Forming Unit over weight, gm. This is the typical measurable unit for microbiologists to present the amounts of living bacteria in defined weights). The publication is available in Can. Vet. J., 2003, 44:212-215. Furthermore, once pets eat the pet foods, pets secreted many different enzymes to help to digest the foods, which are able to destroy the Probiotics viability too. As the foods move down to pet's GI tracts, probiotics have to go through very acidic and high salts environments, especially, in pet's stomach that can be as low as pH 1.0. Most of probiotics will not be able to survive through these harsh environments. In fact the survival percentages of live probiotics is so low that one has to do high numbers of live probiotics for daily oral administration to guarantee the beneficial effects. It is well recognized that the daily oral administration of live probiotics has to be greater than $1 \times 10^{10}$ in human or $1 \times 10^9$ CFU in animals to found the beneficial effects of probiotics. If we convert this amount of probiotics in the best available pet foods described by Canadian scientists, the pets at least have to take more than 10 kg of pet food per day to be able to see the probiotics beneficial effects. Combination of far less numbers of probiotics to feed the pets with the pet natural defense systems in GI tracts, we can easily recognize why the variable effects of probiotics are observed by pet owners. Once pet owners realize to feed the pet with right numbers of live probiotics to the pet, the health benefits of probiotics on the pet will be recognized without doubts.

However, since probiotics are biological entities, delivery of sufficient doses is constantly challenged by inherent factors that might limit their biological activity, including the conditions of growth, processing, preservation, and storage. Specifically, loss of probiotic viability occurs at many distinct stages, including freeze-drying of cells during initial manufacturing, feed preparation (high temperature and high pressure), transportation and storage (temperature fluctuations), and after consumption or in gastrointestinal (GI) track (low pH and bile salts). One of the determined factors for probiotics to have beneficial effects is to maintain the high concentration of viable cells for animals and humans to uptake. Although many commercial probiotic products are available as the additive of animal feed and/or as human functional foods, most of them lose the viability during the manufacturing process, transport, storage and animal feed process (Cinto-Cruce and Gould, 2001). Recently, microencapsulation of probiotics using lipids as the carriers has demonstrated the success for improving the probiotics viability (Pacifico et al., 2001). However, there is relatively little information and progress on microencapsulation of probiotics, especially using biopolymers as the microcarriers.

Microencapsulation, extensively used by pharmaceutical, chemical, and food industries to protect precious and/or active ingredients and ensure proper delivery, is limited to the techniques used (emulsion and extrusion) and the composition of microcarriers, including Na-alginate (also in combination with starch, pectin or whey proteins), gum Arabic (also known as gum acacia), and K-carrageenan (also in combination with locust bean gum). Not only each of the systems has its own limitations, these common systems usually suffer from low mechanical stability. For instance, although alginate is the most commonly used polymer due to its simplicity, low cost, and excellent biocompatibility, the low mechanical strength of the gel makes it highly susceptible to decalcifying and acidification. The microencapsulation using biopolymers greatly enhance the benefit of probiotics as healthful ingredients by retaining sufficient viability and bioactivity under harsh processing conditions during animal feed and pet food production. In addition to improving the shelf life stability, the transportation costs of these microorganisms will also be reduced if the resulting microcapsules could be stored under room temperature.

Microbial exopolysaccharides are classified as biopolymers and are widely used in foods, medicines, and industrial products (Marin, 1998). Microbial biopolymers, unlike other carriers, are capable of forming a three-dimensional structure that is stabilized by cross-links connecting junction zones between individual molecules (Lo et al., 2003). In nature, for example, *Xanthomonas campestris*, a plant pathogen of cabbage, produces xanthan gum as an extracellular slimy material to help the cells attach to their host and to endure environmental stresses. Therefore, application of microencapsulation to bacteria using microbial biopolymers provides a new approach to improve the bacterial viability under harsh environmental conditions.

Studies of GI tract infections have shown that probiotics can modulate the immune response to antigens expressed by GI pathogens (Isolauri 2003). When mice were fed *L. acidophilus* and/or *L. casei* prior to oral challenge with *Salmonella typhimurium*, researchers documented that ~100% of the probiotic-treated group mice survived *S. typhimurium* challenge compared to <20% survival in control animals. Anti-*Salmonella* antibody titers were higher in both the serum and GI tract mucosa of the mice fed *L. acidophilus/L. casei* (Perdigon et al., 1990). Similarly, oral administration of *Bifidobacterium breve* stimulated an improved IgA response to cholera toxin in mice (Yasui et al., 1992), and *L. rhamnosus* GG was shown to increase IgA rotavirus-specific antibody secreting cells in children with acute rotavirus diarrhea (Kaila et al., 1992). Both cellular and humoral immune responses were demonstrated when rotavirus-infected piglets were fed *B. lactis* HN019 (Shu et al., 2001)

Enhanced antibody responses to ovalbumin were demonstrated in gnotobitic mice fed *B. bifidum* (Moreaue et al., 1990). This indicates that probiotics could be used to stimulate an antigen-specific mucosal immune response, and to provide increased protection to non-mucosal sites. Significant increases in IgG anti-influenza antibodies were observed when *B. breve* was fed to mice prior to an oral challenge with influenza vaccine (Yasui et al, 1999). Increased serum IgA titers to *Pseudomonas aeruginosa* were detected in mice fed with *L. casei* (Alvaez et al., 2001). IgA, IgG and IgM antibodies against *E. coli* and rotavirus were found in the feces of piglets fed *Bifidobacterium lactis* HN019 (Shu et al., 2001). Recently, local cell-mediated immunity by *Lactobacillus*-feed, *E. acervulina* infected broiler chickens was demonstrated based on the higher IL-2 secretion and lower *E. acervulina* oocyst production (Dalloul et al., 2003). However, few or no reports related to immune responses were described for lactic acid bacteria other than *Lactobacillus* or *Biofidobacterium*.

Selection through the survival of feces from probiotics-feed chickens.

Strains of lactic acid bacteria differentially stimulate the host immune system. The colonization of the GI tract with probiotic microorganism represents the first step towards establishing a beneficial effect using the introduced bacteria. In order for bacteria to colonize effectively the host, *P. acidilactici*, it must grow in low pH and bile that represent in the GI tract. The strain selection will be emphasized on the isolation of survival strains from feces collected from *P. acidilactici*-feed chickens without inoculation of *Eimeria*. At days 7, 11, 14, 18, and 21, the droppings from *P. acidilactici*-feed chickens will be collected from three individual chickens. Following the similar procedures performed on the droppings from oocysts production, the droppings will be resuspended and soaked in PBS buffer instead of water. The conventional, microbiological culture for determination of the quantitative numbers of colony formation unites (CFU) will be used to isolate the single isolated bacterial colonies and to correlate with the colonization of *P. acidilactici* in chickens. For colonization evaluation, a series of dilutions of homogenized droppings will be plate onto different selective media (such as: MRS media for *P. acidilactici*, Rogosa media for *Lactobacillus* spp, RCA medium for *Clostridium* spp. LB media for *E. coli*) and incubated in different growth conditions. After completing the collection of CFU, hundreds of single colonies isolated from MRS media will be transferred onto fresh MRS media containing 0.9% bile at pH 2.0, which is regarded as the standard GI tract in humans and animals, for further selection of *P. acidilactici*. The transfers will be repeated for two more times onto fresh MRS media containing 0.9% bile at pH 2.0, and the survivals of single colony will be further evaluated by pulse-field gel electrophoresis and API biochemical assays for bacterial strains confirmation before bacteria will be made as the glycerol stock and stored at 70° C.

Strains selection through the colonization of cell lines in vitro.

Adhesion of bacteria to the human cell lines Caco-2 and HT29 has been shown to correlate with lactic acid bacterial colonization in animals (Brassart et al., 1998; Tuomola and Salminen 1998). Further selection of strains that are able to grow at 0.9% bile at pH 2.0 will be selected by the co-cultivation of bacteria with the Caco-2 and HT29 cell lines. Determination for bacterial adhesion to Caco-2 and HT29 cell lines will be confirmed by microscopic examination and will be repeated two more times. Bacteria that can grow at 0.9% bile at pH 2.0 and show the adhesion to Caco-2 and HT29 cell lines will be prepared as highly concentrated probiotics at 10 billion/g for chicken feeding in order to do further screening for bacteria with enhanced immune response in chickens.

Strains selection through oral administration of bacteria to *E. maxima* vaccinated chickens.

To select *P. acidilactici* strains capable of enhancing the immune response of the colonized host, bacteria that adhere effectively to the cell lines will be re-selected in bacteria-feed and *E. maxima* vaccinated chickens. These in vitro and in vivo selection methods would yield *P. acidilactici* strains with enhanced colonization and immune promoting properties in animals. The chickens will be fed with the selected *P. acidilactici* strain, vaccinated with *E. maxima* live oocysts, and infected with high amounts of *E. maxima* sporulated oocysts. The sample collections and the assays for determination of immune responses and disease infection will be the same. The selection cycle will be repeated one more time to confirm the selected strains that have the enhanced immune response properties.

EXAMPLE 1

An eight year old black Labrador hybrid with Beagle and Dalmatian, was fed and observed in Table 1. Symptoms: throws out or daily vomiting, bad body odors, constantly producing and releasing gas with bad odors or flatulence.

Feeding procedure: daily fed a piece of cheese wrapped with a capsule of MITOMAX™, which contains 4 billions CFU of *Pediococcus acidilactici* and *Saccharomyces boulardii*, starting from Jun. 21 to Jul. 4, 2004. MITOMAX™ is a trademark of Imagilin Technology, LLC, Potomac, Md. for gelatin encapsulated probiotics.

TABLE 1

| Date | MITOMAX™ | *Throws out | **Body odors | ***Bad odors of gas release |
|---|---|---|---|---|
| Jun. 19, 2004 | − | Y | +++++ | +++++ |
| Jun. 20, 2004 | − | Y | +++++ | +++++ |
| Jun. 21, 2004 | + | N | +++++ | ++++ |
| Jun. 22, 2004 | + | N | ++++ | ++++ |
| Jun. 23, 2004 | + | N | ++++ | +++ |
| Jun. 24, 2004 | + | N | ++++ | +++ |
| Jun. 25, 2004 | + | N | ++++ | +++ |
| Jun. 26, 2004 | − | Y | ++++ | +++++ |
| Jun. 27, 2004 | + | N | ++++ | ++++ |
| Jun. 28, 2004 | + | N | +++ | +++ |
| Jun. 29, 2004 | + | N | +++ | ++ |
| Jun. 30, 2004 | + | N | +++ | ++ |
| Jul. 1, 2004 | + | N | +++ | ++ |
| Jul. 2, 2004 | + | N | +++ | ++ |
| Jul. 3, 2004 | + | N | ++ | + |
| Jul. 4, 2004 | + | N | ++ | + |

*Y: Observation of throwing-outs or vomiting from the dog N: No observation of throw-outs or vomiting from the dog
**Body odors were determined by the average of three people who objectively smelled the dog twice a day. +++++: very strong odors; ++++: strong odors; +++: somewhat strong odors; ++: less strong odors; + some odors.
***Gas released from dogs were observed and the odors were the average of three people; +++++: very strong odors; ++++: strong odors; +++: some what strong odors ++; less strong odors; + some odors TABLE 1 shows that feeding of a dog daily with probiotics reduced the incidence of vomiting, and reduced odor, in particular, reduced bad body odor, and reduced the incidence of flatulence.

EXAMPLE 2

Eight Chesapeake Bay Retriever dogs aged from 1 to 13 years with different chronic digestive disorders were treated daily by mixing one MITOMAX™ capsule with the morning feeding for 28 days. TABLE 2 shows the results. In TABLE 2 the age of the dogs is in years, the weight is in pounds.

TABLE 2

| Dog | Sex | Age | Initial Weight | Initial Symptoms | Final Weight | Outcome |
|---|---|---|---|---|---|---|
| 1 | M | 9 | 85 | lost appetite | 85 | increased appetite, firm stool |
| 2 | F | 6 | 75 | poor digestion | 75 | digestion improved, firm stool |
| 3 | M | 5 | 86 | loose stool, | 86 | firm stool, |

TABLE 2-continued

| Dog | Sex | Age | Initial Weight | Initial Symptoms | Final Weight | Outcome |
|---|---|---|---|---|---|---|
| 4 | F | 9 | 80 | diarrhea poor digestion, swallowing difficulty | 80 | no diarrhea digestion and swallowing improved |
| 5 | M | 13 | 70 | loose stool, diarrhea | 70 | firm stool, no diarrhea |
| 6 | F | 2 | 68 | lost appetite | 68 | improved appetite |
| 7 | F | 1 | 60 | lost appetite, loose stool, diarrhea | — | improved appetite, firm stool, no diarrhea |
| 8 | F | 9 | 80 | vomiting 2 or 3 times a week | 80 | no vomiting |

TABLE 2 shows that daily feeding dogs of both sexes and a variety of ages with a capsule of probiotics resulted in improvement in digestion, in particular in improvement in appetite, reduction of diarrhea and the improvement in firmness of stools, reduction of swallowing difficulty, and reduction of vomiting.

Microencapsulation of lactic acid bacteria using biopolymers.

Viable lactic acid bacteria and yeasts used in probiotics for pets, such as dogs and cats, are encapsulated and protected by the microbial biopolymers xanthan gum and chitosan. Xanthan gum is a polysaccharide gum which dissolves readily in water with stirring to give highly viscous solutions at low concentrations. It forms strong films on evaporation of aqueous solutions and is resistant to heat degradation. Chitin is a polysaccharide consisting predominately of unbranched chains of N-acetyl-glucosamine residues. Chitosan is deacylated chitin, a polymer often used in water treatment, photographic emulsion, in improving the dyeability of synthetic fibers and fabrics and in wound-healing preparations.

Probiotic microbes were encapsulated with an aqueous solution containing 0.5 to 2.5 percent (weight by volume) xanthan gum and 0.2 to 0.8 percent (weight by volume) chitosan. The pH of the solution was from 2.0 to 7.0. A preferred solution contained 1.25 percent (weight by volume) xanthan and 0.4 percent (weight by volume) chitosan at a pH of 4.15. Viable microbial cells are encapsulated at up to $10^{10}$ colony forming units (cfu) per ml.

Encapsulation of viable probiotic microbes in the mixture of xanthan gum and chitosan has the advantage of protecting the viability of the microbes, of delivering the proper dosage of viable probiotic microbes to the pet or dog which is being fed, and of facilitating the feeding of the probiotic microbes. Dogs and cats do not reject the probiotic microbes when they are encapsulated in a mixture of xanthan gum and chitosan.

Without wishing to be held to this explanation, the inventors suggest the observed efficacy of the chitosan and xanthan gum solution in encapsulation of probiotic microbes is due to the formation of a xanthan-chitosan complex. The mixture of two oppositely charged polyelectrolytes in aqueous solution results in formation of a polyelectrolyte complex due to the electrostatic attraction of oppositely charged polymers. It is postulated that at moderate pH values the xanthan gum is predominately associated with a large number of net negative charges, while chitosan is associated with a large number of net positive charges. The two polymers with opposite net charges therefore bind together forming a stable complex and a strong gel. Relatively high pH values deionize the amino groups on the chitosan with resulting less stable binding between the two polymers and less strong capsule.

Figure 1:
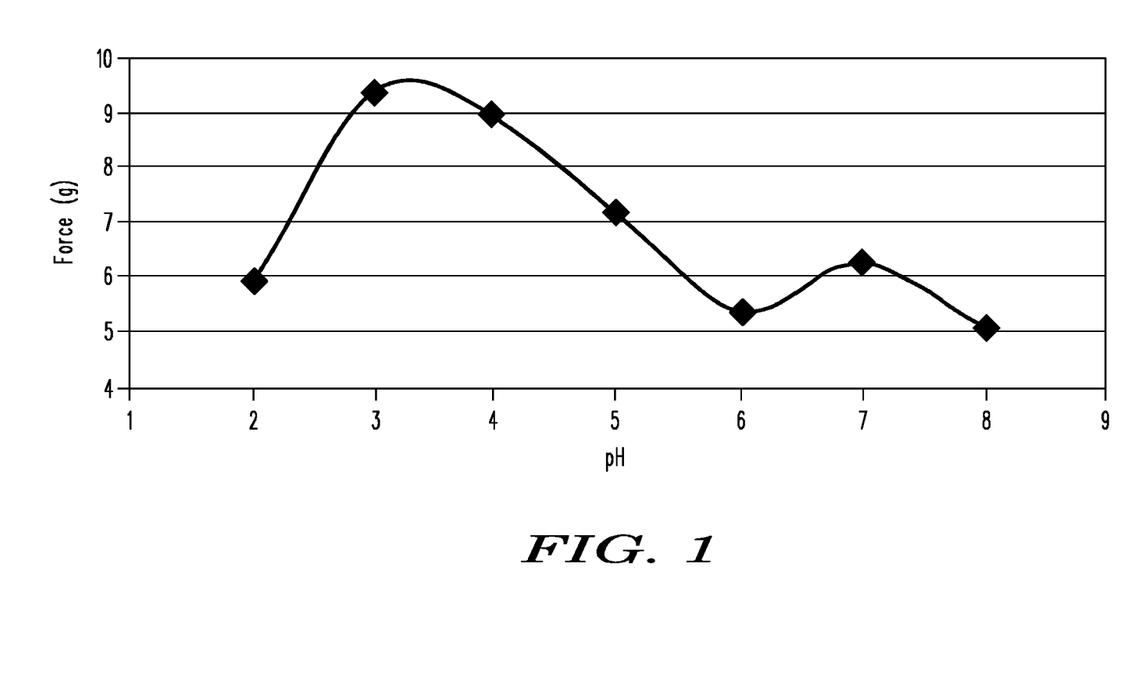
FIG. 1 shows the relationship between pH and capsule hardness.

FIG. 1 is a graph showing the capsule hardness at pH values from 2 to 8. Capsules were formed as in the preferred process above. Capsule hardness or mechanical strength was measured at a variety of pH values using TA.XT2i, using a 5 kg load cell and a distance of 1 mm. FIG. 1 showed that the hardness of the capsules peaks in the pH range of 3 to 4, and was relatively low at pH 6 to 8. The data of FIG. 1 are consistent with the above theoretical discussion of the formation of a chitosan-xanthan gum complex.

Figure 2:
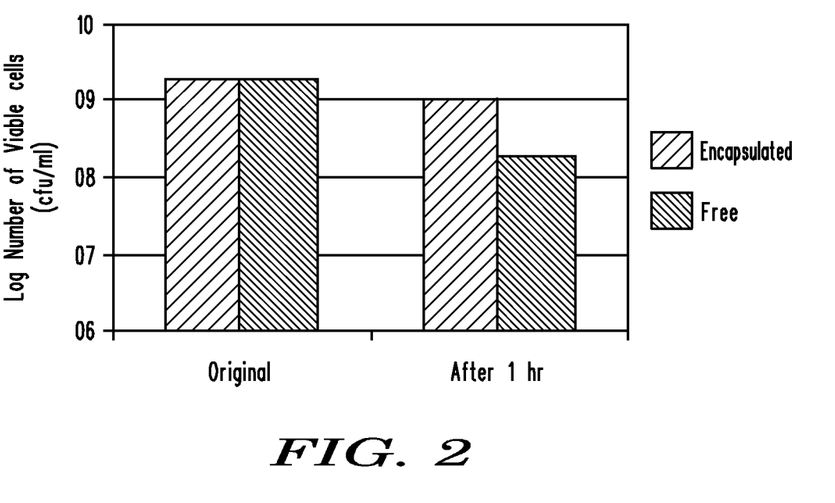
FIG. 2 shows the relationship between viability of encapsulated and unencapsulated probiotic microbes and reduced temperature.

FIG. 2 shows the effect of low temperature on the viability of encapsulated and unencapsulated microbes. Encapsulated and unencapsulated microbes were held for one hour at 0° C. The number of unencapsulated viable microbes declined from about $10^{9.3}$ cfu/ml to about $10^{8.3}$ cfu/ml. The number of encapsulated viable microbes declined from about $10^{9.3}$ cfu/ml to about $10^9$ cfu/ml. FIG. 2 shows the protective effect of encapsulation against low temperature.

Figure 3:
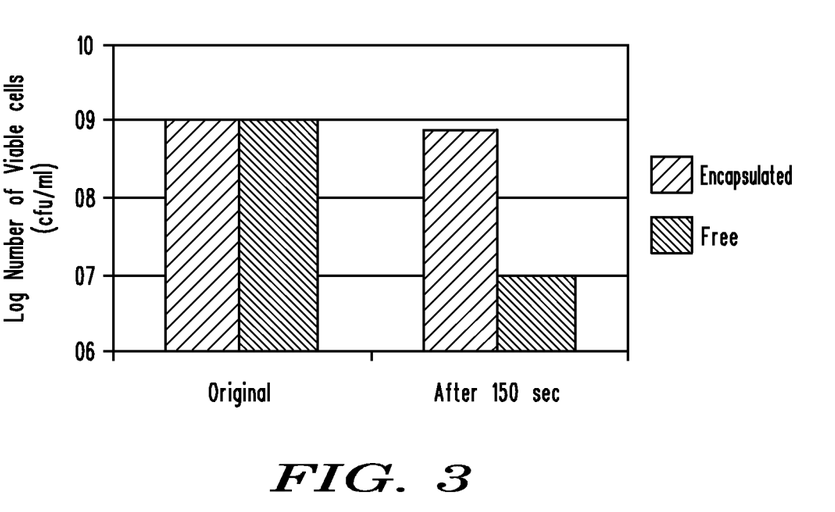
FIG. 3 shows the relationship between viability of encapsulated and unencapsulated probiotic microbes and elevated temperature.

FIG. 3 shows the effect of high temperature on the viability of encapsulated and unencapsulated microbes. Encapsulated and unencapsulated microbes were held for 150 seconds at 60° C. The number of unencapsulated viable microbes declined from about $10^9$ cfu/ml to about $10^7$ cfu/ml. The number of encapsulated viable microbes declined from about $10^9$ cfu/ml to about $10^{8.9}$ cfu/ml. FIG. 3 shows the protective effect of encapsulation against high temperature.

Figure 4:
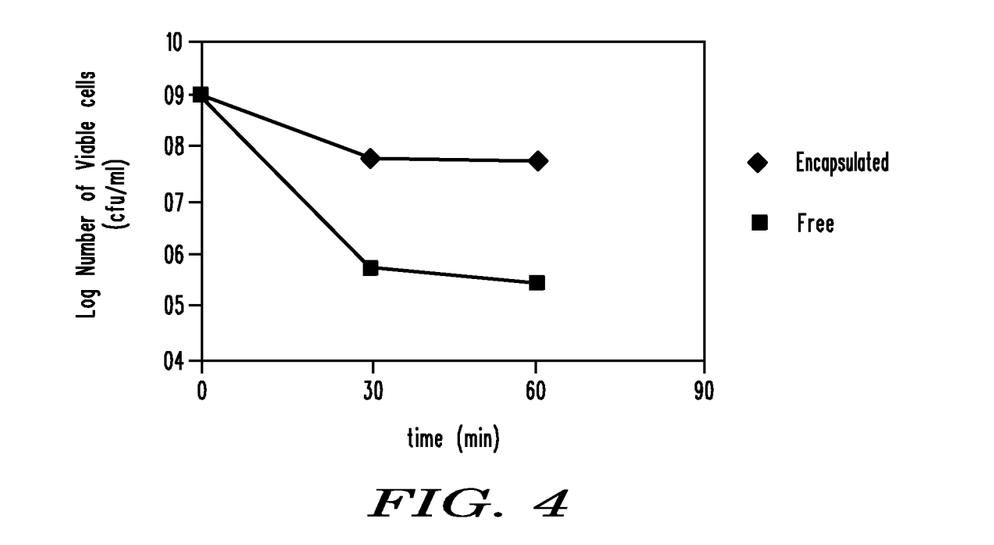
FIG. 4 shows the relationship between viability of encapsulated and unencapsulated probiotic microbes and time of exposure to pH 2.

FIG. 4 shows the effect of low pH on the viability of encapsulated and unencapsulated microbes. Encapsulated and unencapsulated microbes were held from 0 to 60 minutes at pH 2. The number of unencapsulated viable microbes declined from about $10^9$ cfu/ml to about $10^{5.7}$ cfu/ml after 30 minutes and to about $10^{5.5}$ cfu/ml after 60 minutes. The number of encapsulated viable microbes declined from about $10^9$ cfu/ml to about $10^{7.8}$ cfu/ml at both 30 and 60 minutes. FIG. 4 shows the protective effect of encapsulation against low pH.

Probiotics as alternative medicines against infectious parasitic diseases of broiler chickens Avian coccidiosis is the major parasitic disease of poultry causing mortality, malabsorption, inefficient feed utilization, impaired growth rate in broilers and reduced egg production in layers (Lillehoj et al., 2004). The most prominent symptom of avian coccidiosis is growth retardation characterized by reduced weight gains or even weight loss in severe cases, causing a major economic impact to the poultry industry (Dalloul and Lillehoj, 2006). Drugs and live vaccines are the two main control measures of disease; however, due to increasing concerns with prophylactic drug use and high cost of vaccines, alternative control methods are needed. For *Eimeria*-infected-broiler chickens, although the stimulation of antibody production was observed, the increase of cellular immune responses is the key to control the diseases (Dalloul and Lillehoj, 2004). Recent progress in probiotics research demonstrates that live bacteria can influence host humoral immunity against enteric diseases like rotavirus, *E. coli*, and *Salmonella* (Isolauri, E. 2003; Majamaa, et al 1995; Perdigon, et al 2001). In order to apply probiotics as an effective alternative medicine against *Eimeria*-infected broiler chickens one has to show the good effects of both humoral and cellular immunity in probiotics-fed, *Eimeria*-infected broiler chickens.

Examination of potential toxic effects of probiotics on *Eimeria*-infected broiler chickens Day-old broiler chicks were housed in brooders at 15-20 birds per group and fed either control, only commercial feed, or *Pediococcus acidilactici* containing commercial feed from day one. Five diets were formulated based on *Pediococcus acidilactici* levels as percentage of basal feed: 0%, 0.01%, 0.05%, 0.1%, and 0.4%. At day ten, all birds except for the control (no *Pediococcus acidilactici*, no infection) were orally infected with either 5,000 sporulated oocysts of *Eimeria acervulina*. Bird body weights were taken at 0, 6, & 9 days post infection (dpi) and weight gains were calculated. Fecal materials were collected for 4 days, from 6 to 9 days post infection, in small buckets for oocyst counting.

Differences between experimental treatments were tested by variance analysis (ANOVA) using the statistical program GRAPHPAD INSTAT, a trademark for statistical software owned by GraphPad Software, Inc., San Diego, Calif. Differences were considered significant at a probability $P<0.05$. Mean values were then compared by the Dunnett Comparison Test.

Table 3A. Effects of *Pediococcus acidilactici* on growth and on oocysts in the feces from broilers infected with *Eimeria acervulina*.

TABLE 3

| Group | 1 | 2 | 3 | 4 | 5 | 6 |
|---|---|---|---|---|---|---|
| A. Weight gain in grams from 1 to 9 days post infection with 5,000 *Eimeria acervulina* | | | | | | |
| Dose in Oocytes | 0 | 5,000 | 5,000 | 5,000 | 5,000 | 5,000 |
| % *P. acidilactici* | 0 | 0 | 0.01 | 0.05 | 0.1 | 0.4 |
| Av. Weight Gain g. | 396 | 343 | 362 | 366 | 395 | 382 |
| Std. Deviation | 45 | 45 | 51 | 58 | 36 | 44 |
| B. Weight *Eimeria acervulina* oocyte shedding, above groups. | | | | | | |
| Ave. $\times 10^8$ | 0 | 2.65 | 1.97 | 2.39 | 1.39 | 2.10 |
| Std. Deviation | | 0.67 | 0.50 | 0.27 | 0.23 | 0.60 |

Before one can apply any reagents as the potential medicines, elimination of toxic side effects is the crucial before one would apply the reagents for efficacy study. *P. acidilactici* is a natural microorganisms in GI tracts of animals and humans, and has not been described in literature to have significantly toxic effects. To investigate any potential toxic effects of *P. acidilactici* on broiler chickens, we fed broiler chickens or *E. acervulina*-infected chickens 0.01% to 0.4% of *P. acidilactici*. As shown in Table 3A, no weight loss or bird death was observed from the broiler chickens fed only with *P. acidilactici* or those infected with *E. acervulina* and fed with *P. acidilactici*. Furthermore, the *Eimeria*-infected broiler chickens fed with mixtures of probiotics-*P. acidilactici* and *Saccharomyces boulardii* in the 0.01% and 1.0% groups, and *Eimeria acervulina* infected groups showed higher body weight gains during the infection period (Table 3A). For the whole process of experiments, we did not see differences in the major organs (livers, hearts, kidneys, spleens) after feeding the chickens with probiotics. These and similar results demonstrated that *Eimeria* infected broiler chickens showed no detectable morphological differences either fed with *P. acidilactici* up to 40 folds (ranged from 0.01% to 0.4%) or with mixtures of *P. acidilactici* and *S. boulardii* ranging from 0.01% to 1.0%.

Figure 7:
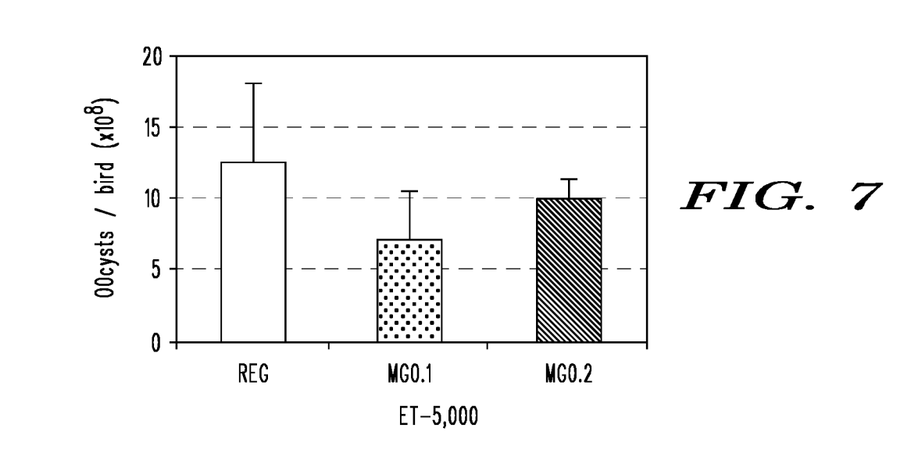
FIG. 7 is a graph of fecal oocytes shed by birds infected by *E. acervulina*.

To demonstrate that *P. acidilactici* can be used against *Eimeria* infected broiler chickens, we fed chickens with/without *P. acidilactici* and then orally infected them with sporulated oocysts of *Eimeria tellena* (*E. tellena*). Interestingly, *E. tellena* infected chickens fed with *P. acidilactici* showed a reduction of oocysts in a range of 20% to 40% from control broiler chickens (FIG. 7). Similarly, we observed the oocysts reduction either in a range of 30% to 50% from broiler chickens infected with *E. acervulina* infected and fed with mixtures of *P. acidilactici* and *S. boulardii* or in a range of 10% to 20% from broiler chickens infected with *E. tellena* and fed with mixtures of *P. acidilactici* and *S. boulardii* (FIG. 8)). These results showed probiotics have the effects on reduction of pathogens or parasites in animals Stimulation of humoral immune responses on *Eimeria*-infected, probiotics-fed broiler chickens.

Figure 5:
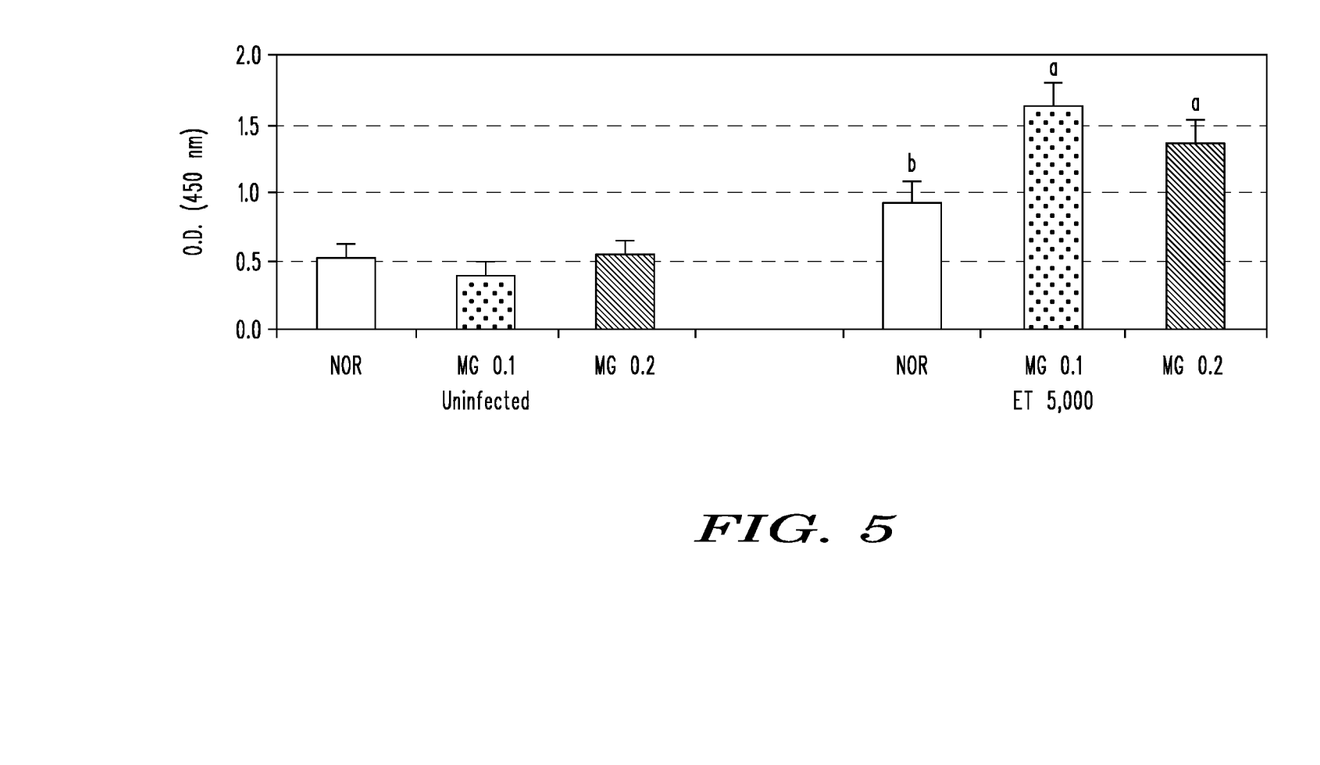
FIG. 5 is a graph showing the effect of probiotics on antibody response.

FIG. 5 shows Anti-EtMIC2 antibody response of broilers fed non-probiotic (NOR), 0.1% or 0.2% Mixtures of *P. acidilactici* and *S. boulardii* supplemented diets for 21 days (MG0.1 and MG0.2 respectively). Birds were either uninfected or infected with 5,000 *E. tennella* oocysts at day 12 post-hatch and sera sampled 10 days post infection. Each bar represents the mean±S.D. (N=3). Means lacking common superscripts differ in uninfected or infected chickens ($P<0.05$).

To assess antibody responses to *Eimeria* antigen, EtMIC2, one of *Eimeria* microneme protein genes that have been cloned and characterized at the molecular level (Dalloul et al, 2006) was used in this study. ELISAs were used to determine the antibody production from serum collected from chickens. Induction of antibody response upon ET infection was evident in all infected groups. Moreover, in *P. acidilactici*-fed birds, significantly ($p<0.05$) higher serum *Eimeria*-specific Ab levels were detected in infected birds when compared to those of birds without probiotics (FIG. 5). These results clearly demonstrate that *P. acidilactici* is able to stimulate humoral immune responses against specific infectious parasites in broiler chickens.

Systemic cellular immune response: Lymphocyte proliferation.

Figure 6:
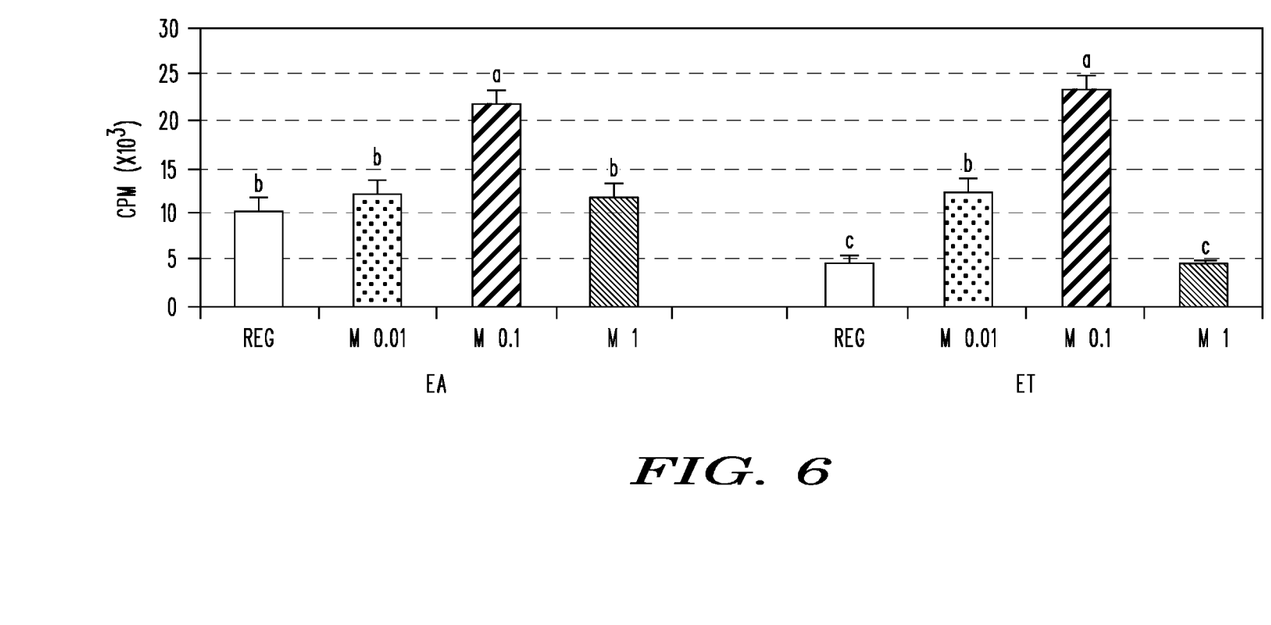
FIG. 6 is a graph showing the effect of probiotics on cellular immune response.

FIG. 6 shows Concanavalin A (ConA) induced proliferation of splenocytes from chickens following treatment with regular, 0.01%, 0.1% or 1.0% M: Mixtures of *P. acidilactici* and *S. boulardii* and infection with *Eimeria*. Birds were infected with 5,000 *E. acervulina* (EA) or *E. tennella* (ET) oocysts at day 14 post-hatch. Splenocytes were collected and cultured in the presence of Con A for 24 h. Cell proliferation was measured by [$^3$H]-thymidine assay. Each bar represents the mean±S.D. (N=3). Means lacking common superscripts differ in EA- or ET-infected chickens ($P<0.05$).

The proliferation responses in splenocytes stimulated with ConA in the birds fed regular or probiotic diets were used to determine systems cellular immune responses against *Eimeria* in *P. acidilactici*-fed broiler chickens. In EA-infected birds, splenocytes of the 0.1% group exhibited significant ($P<0.05$) proliferation rates compared to all other groups including those on the regular and probiotic diets. In the ET-infected groups, 0.01% and 0.1% birds showed significantly ($P<0.05$) higher splenocyte proliferative responses to stimulation with Con A, with higher ($P<0.05$) proliferation rates in 0.1% than 0.01% birds (FIG. 6).

FIG. 7 shows fecal oocysts shed by birds infected with *E. acervulina* (EA). Oocysts were counted in fecal material collected 6-9 dpi with 5,000 *E. tennella* broiler chickens fed regular (REG), 0.1% (MG0.1) or 0.2% (MG0.2) MG: *P. acidilactici*-supplemented diets. Each bar represents the mean±S.D. (N=5 cages).

Figure 8:
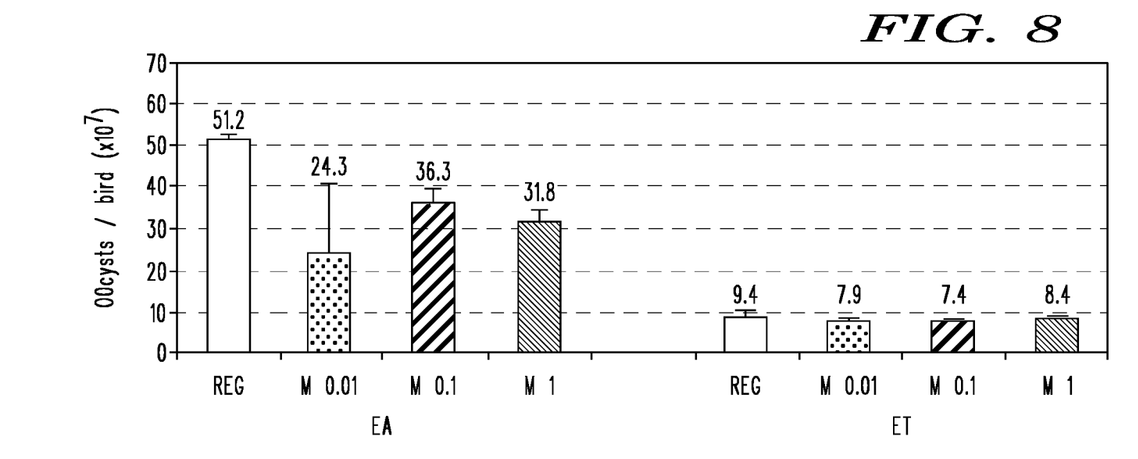
FIG. 8 is a graph of fecal oocytes shed by birds infected by *E. acervulina* or *E. tenella*.

FIG. 8 shows fecal oocysts counted in fecal material collected 6-10 days past infection with 5,000 oocysts *E. acervulina* (EA) or *E. tennella* (ET) Broiler chickens were fed regular (REG), 0.01% (M0.01), 0.1% (M0.1) or 1.0% (M1.0) at day 12 post-hatch. M indicates mixtures of *P. acidilactici* and *S. boulardii*. Each bar represents the mean±S.D. (N=5 cages).

Probiotics as alternative medicines for dogs with digestive disorders or dogs infected by infectious virus Applications of probiotics in dogs with digestive disorders The success of probiotics, MITOMAX™-mixtures of *P. acidilactici* and *S. boulardii*, in *Eimeria* infected broiler chickens led us to perform a field evaluation of canines with digestive disorders. MITOMAX™ is a trademark for probiotics owned by Imagilin Technology, LLC, Potomac, Md. for mixtures of *Pediococcus acidilactici* and *Saccharomyces cerevisiae boulardii* (*S. boulardii*) encapsulated in gelatin capsules. The collaborative field evaluations were performed by four veterinarians in three different animal hospitals located in Sao Paulo, Brazil (Table 4). The dogs' body weight ranged from 2 kg to 26 kg, and age ranged from 1 year old to 15 years old. The dogs suffered from different degrees of digestive disorders and were administered either one or two capsules of probiotics, depending on the dog's body weight. Within 14 days of treatment with probiotics, the dogs recovered from the digestive disorders and showed significant improvement. These results clearly show that probiotics have good effects on canines with digestive disorders.

TABLE 4

Field Evaluation of Probiotics on Dogs with Digestive Disorders in Animal Hospitals of Sao Paulo, Brazil

| Name | Ages (years) | Weight (Kgs) | Sex (M Or F) | Symptoms (D, V, C, OC, F, LA)* before Probiotics treatment** | Length of Probiotics treatment (days) | Effects of Probiotics treatment |
|---|---|---|---|---|---|---|
| Fala Fino | 9 | 16 | F | D+ | 4 | Recovery OK |
| Peinrige | 4 | 10 | M | D+, V+, F+ | 4 | Recovery OK |
| Habil | 9 | 13 | F | OC | 10 | Improved |
| Beiney | 5 | 12 | M | D+, F++ | 9 | Recovery OK |
| Branea | 1 | 4 | F | LA+ | 4 | Improved |
| Pilly | 6 | 12 | M | OC+ | 9 | Improved |
| Focinha | 3 | 9 | M | LA+ | 4 | Improved |
| Nicole | 2 | 6 | F | D+, V+ | 4 | Improved |
| Togriho | 11 | 24 | M | LA+ | 9 | Improved |
| Tata | 10 | 5 | F | D++, F+ | 9 | Recovery OK |
| Rel Deigo | 10 | 25 | M | D+ | 15 | Recovery OK |
| Kate | 2 | 6 | F | D++++ | 7 | Recovery OK |
| Toli | 15 | 26 | M | D++, V++ | 4 | Recovery OK |
| Herna | 13 | 4 | M | D++ | 6 | Recovery OK |
| Mylon | 13 | 4 | M | D++ | 14 | Recovery OK |
| Hyuki | 10 | 4 | F | D++, V++, F+, LA+ | 9 | Recovery OK |
| Pelilico | 2 | 3 | M | D+, F+ | 12 | Recovery OK |
| Drojun | 1 | 7 | M | V+, D++ | 4 | Recovery OK |
| Max | 1 | 2 | M | D++++, F++ | 9 | Recovery OK |

*D: Diarrhea,
V: Vomiting,
C: Constipation,
OC: Body Odor,
F: Flatulence,
LA: loss Appetite;
++++: very severe,
+++: severe,
++: mild to severe,
+: mild
**Probiotics treatment means oral administrated a capsule of MITOMAX ™-mixtures of *P. acidilactici* and *S. boulardii* per day for dog's body weight less than 20 kg, and two capsules of MITOMAX ™ per day for dog's body weight over 20 kg.

Probiotics as alternative medicine to stop bloody diarrhea of parvovirus-infected dogs.

Parvovirus-infected canines develop severe gastrointestinal distress such as vomiting and bloody diarrhea. Without proper treatment, parvovirus-infected dogs can die within a few days. No antibiotics can be applied to cure parvovirus-infected dogs since it is a viral infection. The recovery depends on the canines' ability to develop their own immune systems to fight against virus. This problem is a good candidate for us to apply probiotics to parvovirus-infected dogs. Four dogs diagnosed with parvovirus infection were shown to have bloody diarrhea even after treated with Normosol R, Reglan, Cefazolin, Metronidazole or Ampicillin, +/−Famotidine. Orally administered probiotics included mixtures of *P. acidilactici* and *S. boulardii*, and were given to the four dogs for two to three days. Not only did the bloody diarrhea stop, but also all four dogs had solid stool. No recurrence of bloody diarrhea was reported even after being released from hospital for two weeks as they continued the probiotics treatment (Table 5)

TABLE 5

Effects of probiotics on parvovirus infected dogs

| Name | Age (M) | Weight (Lbs) | Snap parvovirus test | Condition after standard treatment* | Length of probiotics treatment | Effects of Probiotics treatment** | Recurrence of diarrhea in 2 weeks |
|---|---|---|---|---|---|---|---|
| Cali | 4 | 11 | Positive | Bloody diarrhea, >6 times per day | 2 days | Diarrhea stop, solid stool | no |
| Denver | 5 | 14 | Positive | Bloody diarrhea, >6 times per day | 3 days | Diarrhea stop, solid stool | No |
| Flash | 12 | 45 | Positive | Bloody diarrhea, >6 times per day | 2 days | Diarrhea stop, solid stool | No |
| Molie | 9 | 45 | Positive | Bloody diarrhea, >6 times per day | 3 days | Diarrhea stop, solid stool | No |

: Performed by Dr. Volkenbourgh, DVM, at Animal Emergency Clinic, Lancaster, CA.
*Standard parvovirus treatment of the animal emergency clinic includes applying Normosol R, Reglan, Cefazolin, Metronidazole or Ampicillin, +/- Famotidine to the parvovirus infected dogs. Some also received hetastarch or a plasma transfusion.
**Probiotics treatment means oral administrated a capsule of MITOMAX ™-mixtures of *P. acidilactici* and *S. boulardii* per day The effects of probiotics on animals and humans are dependent on the viability of probiotics. Similar numbers of viable probiotics were detected from the encapsulated probiotics, *P. acidilactici*, stored for two years either at room temperature of at 4° C. No significant differences of morphology and body weight were observed by feeding *Eimeria*-infected broiler chickens with *P. acidilactici*, varying from 0.01% to 0.4%. Similar results were obtained when broiler chickens infected with *E. acervulina* or *E. tellena* were fed with mixtures of *P. acidilactici* and *S. boulardii* varying from 0.1% to 1%.

Effects of probiotics, either *P. acidilactici* or mixtures of *P. acidilactici* and *S. boulardii*, on *Eimeria*-infected broiler chickens were determined by 1) the reduction of oocysts isolated from the fecal samples, 2) stimulation of antibody production and 3) stimulation of proliferation of splenocytes. The clinic evaluation of probiotics clearly demonstrated that orally administrated mixtures of *P. acidilactici* and *S. boulardii* has improved the health condition of canines with digestive disorders such as diarrhea, vomiting, appetite loss, and body odor. More importantly, canines suffering from bloody diarrhea caused by parvovirus infection showed recovery after treatment of orally administered mixtures of *P. acidilactici* and *S. boulardii* for two to three days. These results demonstrated that probiotics could be used as alternative medicines against infectious diseases.

Suitable probiotic microbes are yeast and lactic acid bacteria. Suitable probiotic bacteria are *Pediococcus, Lactobacillus, Bifidobacterium, Streptococcus*, and *Enterococcus*. Suitable yeast is *Saccharomyces cerevisiae boulardii*. The encapsulated probiotics are effective against gastrointestinal diseases caused by pathogenic bacteria, viruses, fungi, parasites and single-celled organisms. The encapsulated probiotics are effective against hookworms, roundworms, whipworms and tapeworms. The encapsulated probiotics are effective against coccidians, such as *Giardia*.

Encapsulated probiotics are effective against infectious gastrointestinal diseases in humans when humans with infectious gastrointestinal diseases ingest suitable dosages of encapsulated probiotics. Encapsulated probiotics are effective against infectious gastrointestinal diseases in fish when fish with infectious gastrointestinal diseases ingest suitable dosages of encapsulated probiotics. Probiotics in the form of dry powder are also effective with properties similar to those of encapsulated probiotics.

DRAWINGS

6 Sheets

SEQUENCE LISTING

Not Applicable
IT3
I claim:

1. A method of treating a gastrointestinal infectious disease by enhancing immune responses against antigens in a bird or a mammal, comprising: administering to the bird or mammal infected with said infectious disease an effective amount for said treating a composition comprising at least one probiotic microorganism comprising greater than $1 \times 10^9$ colony forming units of Pediococcus acidilactici encapsulated in a single capsule of gelatin, wherein said infectious disease is caused by protozoa, pathogenic bacteria, fungi, parasites, or a virus selected from the group consisting of parvovirus, rotavirus, and influenza virus and wherein the $1 \times 10^9$ colony forming units of Pediococcus acidilactici encapsulated in the single capsule of gelatin is viable for greater than two weeks.

2. A method of claim 1 wherein the at least one probiotic microorganism is included in animal foods, animal treats, animal flavors, fermented milk products, or yogurts.

3. The method of claim 1, wherein the bird is selected from the group consisting of a chicken, a parrot, a parakeet, a pigeon, a turkey, a duck, and a goose.

4. The method of claim 1, wherein the mammal is selected from the group consisting of a dog, a cat, a guinea pig, a hamster, a mouse, a rabbit, a monkey, a chimpanzee, a pig and a human.

5. The method of claim 1 wherein the parasites are selected from the group consisting of hookworms, roundworms, whipworms and tapeworms.

6. The method of claim 1 wherein the protozoa are selected from the group consisting of Eimeria, Giardia, Cryptosporidum, Toxoplasma, Plasmodium, Leishmania, and Cyclospora.

7. The method of claim 1 wherein treating the infected bird or mammal modulates the immune response of the infected bird or mammal and comprises one or more of increasing antibody production or increasing T cell or helper T-cell proliferation in the infected host.

8. The method of claim 1, wherein the at least one probiotic microorganism is in the form of powder.

9. The method of claim 1, further comprising administering the composition in combination with an antibiotic.

10. The method of claim 1, wherein the composition further comprises Saccharomyces yeast.

* * * * *